July 11, 1967 E. B. BRAUNS Plant Pat. 2,750
APPLE TREE
Filed Feb. 23, 1966
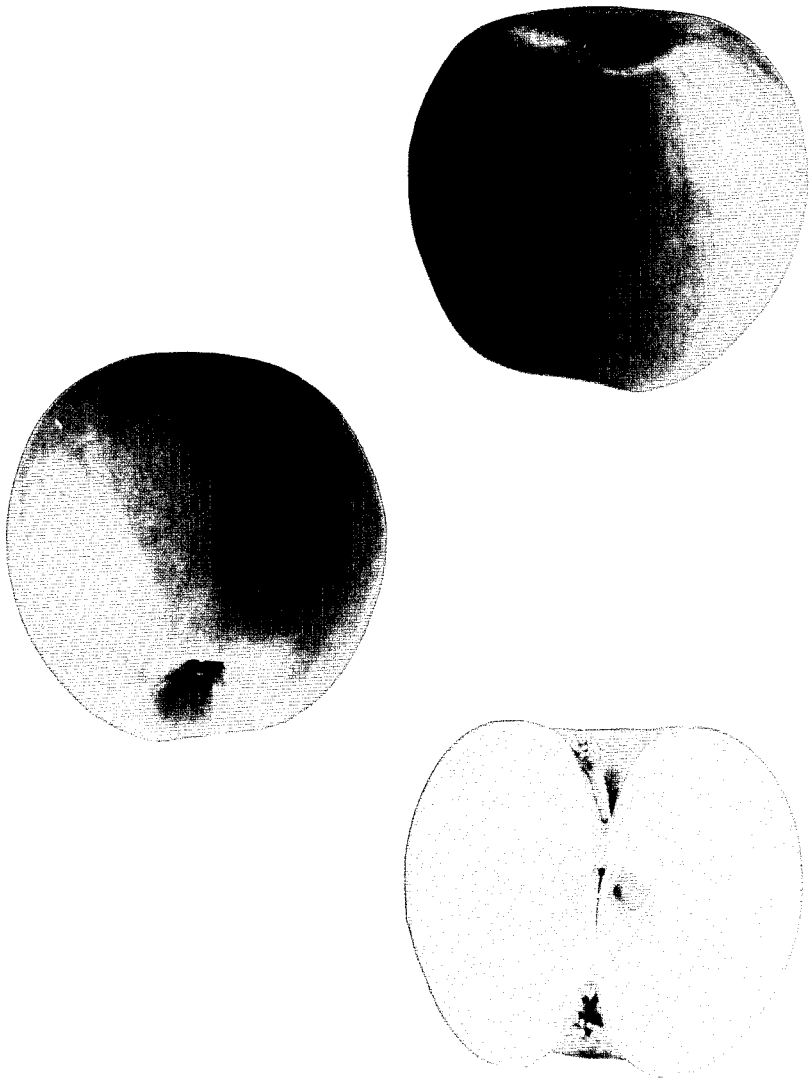
INVENTOR.
EDWARD BARCLAY BRAUNS
BY
Christensen, Sanborn & Matthews
ATTORNEY United States Patent Office Plant Pat. 2,750
Patented July 11, 1967

2,750
APPLE TREE

Edward Barclay Brauns, 913 Idaho St.,
Wenatchee, Wash. 98801

Filed Feb. 23, 1966, Ser. No. 529,620
1 Claim. (Cl. Plt.—34)

This invention or discovery relates to a new and distinct variety of apple tree originally discovered as a volunteer seedling growing at the edge of a commercial orchard of Starking Red Delicious and Black Jonathan (C. and O.) varieties in the Riverside, Wash., area. This new variety is of unknown parentage, but because of its characteristics it is presumed to be a cross between the above two mentioned varieties adjacent to which the original chance seedling was discovered.

In addition to differences in the growth habit and appearance of the tree in comparison with the Starking Red Delicious and the Black Jonathan, this new variety is particularly noteworthy for the early ripening and versatile appeal of its fruit. Crisp, juicy and firm, these apples are highly colored and ripen approximately two weeks before Jonathan. They keep well for an early-maturing variety. Sweeter than the Jonathan, they are more tart than the Delicious, hence are of excellent dessert quality and very flavorful when eaten raw. The fruit keeps well in cold storage and promises to be an outstanding commercial apple not matched by any previously known variety.

The accompanying drawing comprises photographic color prints which show a representative apple of the new variety.

*Tree*

The tree is large, vigorous. Its form is spreading and open. The twigs are slender with long internodes. The bark is a dark reddish-brown, moderately pubescent. Lenticels are numerous, conspicuous, oval to elongated, variable in size, slightly raised. Buds are medium, acute pubescent, appressed. Leaves are medium, rather narrow, not thick; moderately resistant to powdery mildew. Under north central Washington growing conditions the tree blooms approximately May 1st.

*Fruit*

The fruit is of medium size (averaging from 2¾ inches to 3 inches in diameter); form is round-conic, obscurely ribbed; often irregular in shape; sometimes elliptical; frequently unequal-sided. The stem is short to very short, green; often thickened at the free end. The cavity is wide, acute, deep; often greenish; occasionally slightly russeted; russet rays sometimes present. Calyx is closed; lobes often moderately reflexed at tips. The basin is wide, medium-deep; sides abrupt to sloping; often distinctly furrowed; pubescent. Skin is tough; dots are numerous, distinct, sunken; light yellow undercolor; medium to dark red blush (Munsell hue 5R4/12; ISCC–NBS designation: strong red, as referenced to Nickerson Color Fan); lighter-colored fruits distinctly streaked with darker reds; suture line occasionally present. Calyx tube is funnel-shaped; stamens median. Core of medium size; position median; cells symmetrical, open; core lines clasping. Carpels broadly cordate, tufted. Seeds are medium size, light brown, plump, acute. Flesh is tinged with yellow, firm, very crisp, juicy, sub-acid; quality very good. Fruit ripens approximately two weeks before Jonathan and is of excellent dessert quality; keeps well for an early-maturing variety.

The new variety has been asexually propagated at the Irrigated Agriculture and Extension Center, Prosser, Wash., and at the orchard of the Keystone Fruit Company near Entiat, Wash., with the result that the above-described distinguishing characteristics have proved to be stable.

Having thus disclosed my improved variety, I claim:

A new and distinct variety of apple tree as shown and described.

No references cited.

ABRAHAM G. STONE, *Primary Examiner.*

ROBERT E. BAGWILL, *Examiner.*